US006479057B2

(12) United States Patent
Allwohn et al.

(10) Patent No.: US 6,479,057 B2
(45) Date of Patent: Nov. 12, 2002

(54) COSMETIC COMPOSITIONS CONTAINING INORGANIC-ORGANIC HYBRID PREPOLYMERS AND METHODS OF TREATING HAIR, SKIN OR NAILS USING SAME

(75) Inventors: Juergen-Andreas Allwohn, Riedstadt (DE); Susanne Birkel, Rossdorf (DE); Angelika Beyer, Waldaschaff (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/367,338

(22) PCT Filed: Dec. 1, 1998

(86) PCT No.: PCT/EP98/07794

§ 371 (c)(1),
(2), (4) Date: Aug. 11, 1999

(87) PCT Pub. No.: WO99/33434

PCT Pub. Date: Jul. 8, 1999

(65) Prior Publication Data

US 2002/0037298 A1 Mar. 28, 2002

(30) Foreign Application Priority Data

Dec. 23, 1997 (DE) .......................................... 197 57 455
May 20, 1998 (DE) .......................................... 198 22 722

(51) Int. Cl.$^7$ .......................... A61K 7/00; A61K 31/47; A61K 7/06; A61K 7/11; A61K 7/09
(52) U.S. Cl. ................. 424/401; 424/70.12; 424/70.19; 424/70.21; 424/70.22; 424/70.27; 424/70.28; 424/78.02; 424/70.1
(58) Field of Search .............................. 424/70.1, 70.11, 424/70.12, 61, 70.19, 70.21, 70.22, 70.27, 70.28, 70.29, 78.02, 47, 401

(56) References Cited

U.S. PATENT DOCUMENTS 5,616,598 A * 4/1997 Lion et al. ................... 514/374
5,650,159 A * 7/1997 Lion et al. ................... 424/401

FOREIGN PATENT DOCUMENTS

| EP | 38 28 098 A1 | 3/1990 |
| EP | 0 526 875 A1 | 2/1993 |
| EP | 0 580 488 A1 | 1/1994 |
| EP | 0 610 831 A2 | 8/1994 |
| EP | 0 647 664 A1 | 4/1995 |
| EP | 0 792 846 A1 | 9/1997 |
| WO | 95/13855 | 5/1995 |

OTHER PUBLICATIONS

Fraunhofer–Institut Fuer Silicatforschung (ISC), Taetigkeitsbericht 1993, pp. 51–60.
Sintesis Y Preparacoin De Materiales Hibridos Organico/Inorganico. Ormoceros. Nuevas Aplicaciones De Los Materiales Polimeros', By Barrales–Rienda, Revista de Plasticos Modernos, N. 483, Sep. 1996, pp. 257–274.
"Ormocer: Neuer Korrosionsschutz Fuer Messingoberflaechen", Jahrbuch Oberflaechentechnik (1993), 49, pp. 243–251.

* cited by examiner

Primary Examiner—Thurman K. Page
Assistant Examiner—S. Tran
(74) Attorney, Agent, or Firm—Michael J. Striker

(57) ABSTRACT

The hair treatment method includes applying to hair an effective amount of aqueous, alcoholic or aqueous-alcoholic hair treatment composition containing from 0.05 to 15 percent by weight of at least one as-yet-uncrosslinked hydrolytic precondensation product for forming an inorganic-organic hybrid polymer and optionally at least one film-forming hair-setting polymer, and subsequently crosslinking the as-yet-uncrosslinked hydrolytic precondensation product while the as-yet-uncrosslinked hydrolytic precondensation product remains on the hair to form the inorganic-organic hybrid polymer in order to provide long-lasting good hair setting. The hydrolytic precondensation product has an Si—O—Si network and is made by hydrolytically condensing at least one organosilane having crosslinkable groups with or without a network-modifying compound for modifying the crosslinking of the crosslinkable groups.

14 Claims, No Drawings

COSMETIC COMPOSITIONS CONTAINING INORGANIC-ORGANIC HYBRID PREPOLYMERS AND METHODS OF TREATING HAIR, SKIN OR NAILS USING SAME

BACKGROUND OF THE INVENTION

The subject matter of the invention includes cosmetic compositions containing at least one inorganic-organic hybrid prepolymer and methods of treating hair, skin or nails using inorganic-organic hybrid prepolymers or crosslinked inorganic-organic hybrid polymers.

People have always considered an attractive external appearance to be important. The hair-do plays a special role in this respect. The basis for an attractive external appearance is well-groomed and well cared-for hair. There are many known products which by means of added polymers confer to hair good hold, volume, elasticity, springiness and sheen. These styling products, for example in the form of gels, facilitate shaping, as sprays they improve the firmness and as foaming fixatives they improve the hair volume. Moreover, besides good hold, natural springiness and elasticity, styling products confer to hair a natural sheen.

Hair fixatives and hair-care agents usually consist of solutions of film-forming synthetic or natural polymers. Suitable synthetic polymers are, for example, polyvinylpyrrolidone, polyvinylpyrrolidone-polyvinyl acetate copolymers and polyacrylic or polymethacrylic acid polymers. Useful natural polymers include, for example, shellac, gelatin, chitosan salts, polysaccharides and derivatives thereof and cellulose derivatives.

In terms of hair-conditioning and particularly hair-setting properties, however, not all the aforesaid substances are as yet fully satisfactory. Their drawbacks manifest themselves, for example, in that it is very difficult to meet all or several of the desired requirements at the same time and that conventional polymers are washed out of the hair after only one washing. As a result, the volume and hair-do disappear completely, and a new hair-do is required.

SUMMARY OF THE INVENTION

Hence, a need exists to further improve the hold, elasticity, springiness, feel and sheen of human hair. According to the invention, this objective can be reached by use of inorganic-organic hybrid prepolymers which after being applied to the hair are crosslinked to form inorganic-organic hybrid polymers.

We have found that inorganic-organic hybrid prepolymers can also be used in cosmetic agents and that marked improvement can be achieved in agents intended to produce longer-lasting hair-dos and hair grooming if they contain at least one inorganic-organic hybrid prepolymer. By crosslinking the prepolymers on the hair, the resulting polymers are more strongly linked with the hair and, hence, can better stabilize the hair-do. By an appropriate choice of the polymers, it is also possible to confer to the hair a good feel and sheen besides good hold.

The inorganic-organic hybrid polymers formed by the crosslinking of the prepolymers in accordance with the invention are also known under the name ORMOCER® (organic modified ceramics). These are silicone polymers occupying a special place between the classical glasses defined as inorganic glasses (silicates) and crosslinked organic polymers. The hybrid polymers can be prepared by a method known as the sol-gel process and they are known as coating materials for metals, glass, stone, polymers etc (Fraunhofer-Institut für Silicatforschung [Fraunhofer Institute for Silicate Research] (ISC), Progress Report, pages 51 to 60 and literature references cited therein). Other reviews concerning the preparation, use and properties of inorganic-organic hybrid polymers can be found in "Sintesis y preparacion de materiales hibridos organico/inorganico. Ormoceros. Nuevas aplicaciones de los materiales polimeros"; [Synthesis and Preparation of Organic/inorganic Hybrid Materials. Ormocers. New Applications of Polymeric Materials], Revista de Plasticos No.483, September 1996, pp.257–274, and literature references cited therein, as well as in "ORMOCER": Neuer Korrosionsschutz für Messingoberflächen" [ORMOCER: A New Corrosion Inhibitor for Brass Surfaces], Jahrbuch Oberflächentechnik (1993), 49, pp. 243–251.

Processes for the preparation of inorganic-organic hybrid polymers and prepolymers and their use as coating materials for, among other things, metal surfaces or fabrics made of natural fibers are described, for example, in German Unexamined Patent Application DE-OS 38 28 098, EP 0 526 875, EP 0 580 488, EP 0 610 831, EP 0 792 846 and WO 95/13855.

The synthesis of hybrid prepolymers is based on the use of functionalized silanes having general formula (I)

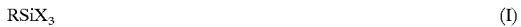

$$RSiX_3 \qquad (I)$$

wherein X denotes a hydrolyzable and condensable group and R stands for a crosslinkable organic group. First, hydrolytic precondensation affords the inorganic Si—O—Si network which is then crosslinked further by reactions of the crosslinkable organic R groups.

By hybrid prepolymers in the sense of the present invention are meant products obtained by precondensation and which are not yet crosslinked through the R groups.

The crosslinkable R group usually denotes an aliphatic side group which can contain various functional groups, such as amino, epoxy, hydroxyl, methacrylate or other polymerizable groups. In particular, R can be selected from among alkyl, alkenyl, alkynyl, aryl, arylalkyl, alkylaryl, arylalkenyl, alkenylaryl, arylalkynyl or alkynylaryl groups. The R group can be interrupted by O, S or N atoms and, if it is not in itself polymerizable, contains at least one crosslinkable substituent from the group consisting of halogens, amino, amido, aldehyde, keto, alkylcarbonyl, carboxy, mercapto, cyano, hydroxy, alkoxy, methacryloxy, epoxy or vinyl groups.

The X groups can denote, independently of each other, alkoxy, aryloxy, acyloxy, alkylcarbonyl or alkoxycarbonyl groups, halogen, hydrogen or a substituted or unsubstituted amino group. Ethoxy and methoxy groups are particularly preferred.

In particular, the silane of formula (I) can be selected from among vinyltrialkoxysilanes, vinyltriacetoxysilanes, aminopropyltrialkoxysilanes, isocyanatopropylalkoxysilanes, mercaptopropyltrialkoxysilanes, vinyltrichlorosilane, allyltrialkoxysilanes, allyltriacetoxysilane, 3-isocyanatooxypropyltrialkoxysilanes, methacryloxypropenyltrialkoxysilanes, 3-methacrylocarbonyloxypropyltrialkoxysilanes, 3-cyanopropyltrialkoxysilanes, 4-mercaptobutyltrialkoxysilanes, 6-mercaptohexyltrialkoxysilanes, 3-mercaptopropyltrialkoxysilanes, 3-(ethylenediamino)

propyltrialkoxysilanes, 3-(diethylenetriamino)
propylalkoxysilanes, 3-glycidoxypropyltrialkoxysilanes,
2-[4-(1,2-epoxycyclohexyl)]ethyltrialkoxysilanes and
3-(trialkoxysilyl)propylsuccinic anhydride, wherein the
alkoxy groups denote methoxy or ethoxy groups.
3-Glycidoxypropyltrialkoxysilanes and
3-mercaptopropyltrialkoxysilanes are particularly preferred.

Precondensed silane oligomers soluble in the reaction
mixture can be used in place of the monomeric starting
silanes. Fluorinated silane derivatives can also be used.

The compounds of general formula (I) can be combined
with metal compounds, for example with the alkyl, alkoxy,
halogen, acyloxy, hydroxy, oxyhalogen or hydroxyhalogen
compounds of titanium, zirconium or aluminum as well as
with other network-modifying compounds, for example
those of formula $SiX_4$ (II) or compounds of formula
$SiR'X_2R$ (III), wherein R' denotes a non-crosslinkable, non-
condensable alkyl or aryl group, and R and X have the
afore-indicated meaning.

The network-modifying compounds, for example in the
case of compounds of formula (II), can bring about an
increase or, in the case of compounds of type (III) a
decrease, in the degree of crosslinking in the inorganic part.

In particular, the metal compounds of the transition
metals, particularly those of subgroup IV, preferably Ti or Zr
compounds, or of main groups III or IV, preferably alumi-
num compounds, can be selected from among titanium
tetrachloride, tetraalkoxytitanium, zirconium tetrachloride,
tetraalkoxyzirconium, dichlorozirconium oxide,
trialkoxyaluminum, dihydroxyaluminum chloride, tribu-
toxyaluminum and tetrapropoxyzirconium, wherein alkoxy
stands for methoxy, ethoxy, isopropoxy, n-propoxy, butoxy
or 2-ethylhexoxy.

In particular, the compound of formula (II) can be selected
from among tetramethoxysilane, tetraethoxysilane,
trimethoxysilane, tetra-n-propoxysilane or
tetraisopropoxysilane, tetrabutoxysilane, tetrachlorosilane,
trichlorosilane and tetraacetoxysilane.

Other network-modifying compounds can be selected
from among methyltrichlorosilane, methyltrialkoxysilanes,
ethyltrichlorosilane, ethyltrialkoxysilanes,
propyltrialkoxysilanes, phenyltrialkoxysilanes,
dimethyldichlorosilane, dimethyldialkoxysilanes,
dimethyldihydrosilane, diphenyldichlorosilane,
diphenyldialkoxysilanes, tripropylhydroxysilane,
4-aminobutylmethyidialkoxysilanes,
aminomethyldimethylalkoxysilanes,
vinylethyidichlorosilane, vinylmethyldiacetoxysilane,
vinylmethyidichlorosilane, vinylmethyldialkoxysilanes,
phenylvinyldialkoxysilanes, phenylvinyldialkoxysilanes,
phenylallyidichlorosilane,
4-aminobutylmethyidialkoxysilanes, aminomethyidimethy-
lalkoxysilanes and comparable compounds, wherein the
alkoxy groups are preferably methoxy or ethoxy groups.

The preparation and the use of inorganic-organic hybrid
polymers involves hydrolysis of the starting compounds to
form a colloidal solution which contains the cleaved-off
hydrolysis products, for example the alcohols, and which is
also referred to as the coating material. This coating material
is either applied directly to the substrate (for example to the
hair, skin or nails) or it can be incorporated into conventional
cosmetic agents. In a second step, following the formation of
the inorganic Si—O—Si network, the organic molecular
groups are crosslinked with each other. This can be accom-
plished by conventional polymerization reactions, for
example by reactions involving double bonds. Polyaddition
reactions, such as those occurring with epoxy resins, can
also be used to crosslink organic side chains.

Preferably, the precondensation is carried out in the
presence of a condensation catalyst. Suitable condensation
catalysts are proton- and hydroxyl ions-eliminating com-
pounds and amines. German Unexamined Patent Applica-
tion DE-OS 38 28 098 deals with a process based on
precondensation. The present invention includes the con-
densation catalysts mentioned in that application.

The inorganic-organic hybrid prepolymers can be used for
hair treatment by subjecting, in a first step, at least one
organofunctional silane of formula (I) to hydrolytic
precondensation, optionally in the presence of at least one
condensation catalyst, and then, in a second step, crosslink-
ing it to form the hybrid polymer. Crosslinking can be
induced by the action of heat, light or a suitable polymer-
ization catalyst and is preferably carried out after the mate-
rial has been applied to the hair.

Hybrid prepolymers in the form of an inorganic network
(precondensation product of the first reaction step) can be
incorporated into aqueous, alcoholic or aqueous/alcoholic
hair-setting and hair-care agents and thus applied to the hair.
By exposure to heat, the organic network is then formed on
the hair thus setting the hair-do. Depending on the properties
of this polysiloxane, a more stable or better-groomed hair
with a pleasant, natural feel and considerable sheen is
obtained.

Preferred systems for the formation of inorganic-organic
hybrid polymers are the following:

1) 3-glycidoxypropyltrimethoxysilane,
3-triethoxysilylpropylsuccinic anhydride and
1-methylimidazole, preferably in a weight proportion of
45–65:30–45:1, for example 57.4:36.9:1;

2) 3-glycidoxypropyltrimethoxysilane, trimethoxyphenylsi-
lane and aminosilane, for example
aminopropyltriethoxysilane, tributoxyaluminum and
ethyl acetoacetate, preferably in a weight proportion of
1–2:1.5–2.5:1:4–5:2–3, for example 1.4:1.8:1:4.45:2.75.

3) 3-glycidoxypropyltrimethoxysilane, tetramethoxysilane,
tributoxyaluminum, tetrapropoxyzirconium and
triethanolamine, preferably in a weight proportion of
4.5–5.5:2–3:0.8–1.8:1.7–2.5:1, for example
5.1:2.5:1.2:2.1:1;

4) 3-glycidoxypropyltrimethoxysilane,
trimethoxyphenylsilane, 2,2,2-trifluoroethylamine, tribu-
toxyaluminum and ethyl acetoacetate, preferably in a
weight proportion of 13–16:1.5–2.5:1:3–5:2–3.5, for
example 14.4:1.9:1:4.0:2.6;

5) 3-methacryloxypropyltrimethoxysilane and
tetrapropoxyzirconium, preferably in a weight ratio of
2–3.5:1, for example 2.6:1, with a UV or thermal initiator;

6) 3-glycidoxypropyltrimethoxysilane,
trimethoxyphenylsilane, aminosilane, for example
aminopropyltriethoxysilane, tributoxyaluminum and
ethyl acetoacetate, preferably in a weight proportion of
6–9:1:0.8–1.5:2–3:1–2, for example 7.2:1:1.1:2.5:1.3;

7) 3-glycidoxypropyltrimethoxysilane,
trimethoxyphenylsilane, aminosilane, for example
aminopropyltriethoxysilane, tributoxyaluminum and
tetrapropoxyzirconium, preferably in a weight proportion
of 9–10.4:3.8–4.5:1:0.8–2.8:3–5, for example
9.6:4.1:1:2.2:3.9;

8) 3-glycidoxypropyltrimethoxysilane, aminosilane, for
example aminopropyltriethoxysilane and
3-mercaptotriethoxysilane, preferably in a weight propor-
tion of 18–21:1:6.5–8, for example 19.2:1:7.2;

9) mercaptopropyltriethoxysilane and hydrochloric acid (1
N) in a molar ratio of, preferably, 1:1–2, for example
1:1.5;

10) 3-glycidoxypropyltrimethoxysilane, trimethoxyphenylsilane, tributoxyaluminum and ethyl acetoacetate, preferably in a weight proportion of 5–6:1–2:1–2.5:1, for example 5.4:1.5:1.9:1.

11) mercaptopropyltriethoxysilane and vinyltriethoxysilane, preferably in a weight ratio of 1–2:1, for example 1.25:1, and aqueous hydrochloric acid (1 N).

Systems 3), 9) and 11) are particularly preferred.

Advantageously, the inorganic-organic hybrid polymer or prepolymer can also be used as a carrier for active or auxiliary cosmetic or pharmaceutical ingredients, for example antidandruff products, dyes or pigments. To this end, the active or auxiliary ingredients can be either physically incorporated or chemically bound.

Another object of the invention is a process for hair treatment whereby a) a not-as-yet-crosslinked precondensation product of an inorganic-organic hybrid polymer in an appropriate cosmetic base is applied to the hair and b) subsequently crosslinked to form the hybrid polymer.

To this end, the crosslinking can be induced by heat, light or a polymerization initiator. Suitable initiators are, for example, 1-hydroxycyclohexyl phenyl ketone or tert.butylperoxy 2-ethylhexanoate. Thermally induced crosslinking is carried out at 20 to 80° C., preferably at 40 to 50° C. and particularly at 40 to 50° C., preferably for 2 to 20 minutes.

Yet another object of the present invention are cosmetic agents containing at least one inorganic-organic hybrid prepolymer in an appropriate cosmetic base. In a cosmetic agent according to the invention, the hybrid prepolymer is contained in an amount from, preferably, 0.01 to 40 wt % and particularly in an amount from 0.05 to 15 wt %, in an appropriate cosmetic base.

In general, the agent according to the invention is used as an aqueous, alcoholic or aqueous-alcoholic solution. Suitable solvents are, for example, aliphatic alcohols with 1 to 4 carbon atoms or a mixture of water and one of said alcohols. Other organic solvents can also be used, among them, in particular, unbranched or branched hydrocarbons, such as pentane, hexane, isopentane and cyclic hydrocarbons such as cyclopentane and cyclohexane. The solvent is used in an amount from 0.5 to 99 wt % and preferably from 40 to 90 wt %.

In a particular embodiment of the invention, the inorganic-organic hybrid prepolymer is used together with at least one film-forming and hair-setting polymer. The film-forming and hair-setting polymer can be of synthetic or natural origin and have a nonionic, cationic, anionic or amphoteric character. Such an added polymer which in the hair-treating agent is present in an amount from 0.01 to 50 wt %, preferably from 0.01 to 20 wt % and particularly rom 0.1 to 15 wt %, can also consists of a mixture of several polymers and can, by addition of other polymers exerting a thickening action, be modified in terms of its hair-setting properties.

According to the invention, by film-forming, hair-setting polymers are meant polymers which when used in a 0.01 to 5% aqueous, alcoholic or aqueous-alcoholic solution are capable of depositing a polymer film onto the hair thus setting the hair.

Suitable synthetic nonionic, film-forming, hair-setting polymers that can be used in the hair-treating agent according to the invention are homopolymers of vinylpyrrolidone, homopolymers of N-vinylformamide, copolymers of vinylpyrrolidone and vinyl acetate, terpolymers of vinylpyrrolidone, vinyl acetate and vinyl propionate, polyacrylamides or polyethylene glycols with a molecular weight of 800 to 20,000 g/mole.

The suitable synthetic film-forming anionic polymers include crotonic acid-vinyl acetate copolymers and the terpolymers of acrylic acid, ethyl acrylate and N-tert.butylacrylamide.

Natural film-forming polymers or polymers derived therefrom by chemical modification can also be used in the hair-treating agents according to the invention. Useful in this respect are low-molecular-weight chitosan with a molecular weight of 30,000 to 70,000 g/mole, or high-molecular-weight chitosan, mixtures of oligo- mono- and disaccharides, Chinese gum rosin, cellulose derivatives such as hydroxypropylcellulose with a molecular weight of 30,000 to 50,000 g/mol, or shellac in neutralized or un-neutralized form.

Amphoteric polymers can also be used in the hair-treating agents of the invention. Suitable are, for example, copolymers of octylacrylamide, tert.butylaminoethyl methacrylate and two or more monomers from the group consisting of acrylic acid, methacrylic acid and derivatives thereof.

Suitable cationic polymers that can be used according to the invention are the copolymers of vinylpyrrolidone and the quaternized derivatives of dialkylaminoacrylates and methacrylates, for example vinylpyrrolidone-dimethylaminomethacrylate copolymers quaternized with diethyl sulfate. Other suitable cationic polymers are, for example, the copolymer of vinylpyrrolidone and vinylimidazolium methochloride, the terpolymer of dimethyidiallylammonium chloride, sodium acrylate and acrylamide, the terpolymer of vinylpyrrolidone, dimethylaminoethyl methacrylate and vinylcaprolactam, the quaternized ammonium salt prepared from hydroxyethylcellulose and a trimethylammonium-substituted epoxide, the vinylpyrrolidone-methacrylamidopropyltri methylammonium chloride copolymer and diquaternary polydimethylsiloxanes.

The consistency of the hair-treating agents according to the invention can be increased by addition of a thickener. Suitable for this purpose are, for example, the homopolymers of acrylic acid having a molecular weight of 2,000,000 to 6,000,000 g/mole. Also suitable are the copolymers of acrylic acid and acrylamide (sodium salt) with a molecular weight of 2,000,000 to 6,000,000 g/mole and sclerotium gum. Copolymers of acrylic acid and methacrylic acid are also suitable.

Usually, other known cosmetic additives can be added to the hair-treating agent according to the invention, for example nonsettting nonionic polymers, such as polyethylene glycol with a molecular weight of about 600 g/mole, nonsetting anionic and natural polymers as well as mixture thereof, in an amount of, preferably, 0.01 to 50 wt %. It is also possible to add perfumes in an amount from 0.01 to 5 wt %, opacifiers such as ethylene glycol distearate in an amount from 0.01 to 5 wt %, wetting agents or emulsifiers belonging to the classes of anionic, cationic, amphoteric or nonionic surfactants, such as fatty alcohol sulfates, ethoxylated fatty alcohols, fatty acid alkanolamides and the esters of hydrogenated castor fatty acids in an amount from 0.1 to 30 wt %, moreover humectants, dyes, light stabilizers, anti-oxidants and preservatives in an amount from 0.01 to 10 wt %.

The hair-treating agents according to the invention can also be improved by addition of conventional silicone polymers, for example polydimethylsiloxane (INCI: dimethicone), α-hydro-ω-hydroxy-polyoxydimethylsilylene (INCI: dimethiconol), cyclic dimethylpolysiloxane (INCI: cyclomethicone), trimethyl(octadecyloxy)silane (INCI: stearoxytrimethylsilane), dimethylsiloxane/glycol copolymer (INCI: dimethicone copolyol), dimethylsiloxane-aminoalkylsiloxane copolymer with hydroxyl end groups (INCI: amodimethicone), monomethylpolysiloxane with lauryl side chains and polyoxyethylene and/or polyoxypropylene terminal blocks (INCI: laurylmethicone copolyol), dimethylsiloxane-glycol copolymer acetate (INCI: dimethicone copolyol acetate) and dimethylsiloxane-aminoalkylsiloxane copolymer with trimethylsilyl end groups (INCI: trimethylsilylamodimethicone). Preferred silicone polymers are dimethicone, cyclomethicone and dimethiconol). Mixtures of silicone polymers are also suitable, for example a mixture of dimethicone and dimethiconol.

The names given in parenthesis are those of the INCI (International Cosmetic Ingredients) nomenclature developed for the naming of cosmetic active and auxiliary ingredients.

The agents according to the invention can be used in different application forms, for example in aerosol preparations, as foams or sprays, or as a non-aerosols which are used by means of a pump or as a "pump and spray". The use of common oil-in-water [O/W] and water-in-oil [W/O] emulsions is also possible as is the use in application forms such as lotions, milk, liquid fixatives, creams, gels, foaming gels, waxes or microemulsions.

The agents according to the invention can also be formulated as coloring or grooming hair-treating agents, for example as color fixatives and hair rinses.

When the agent of the invention is in the form of an aerosol hair spray or aerosol hair coating, it contains additionally 15 to 85 wt % and preferably 25 to 75 wt % of a propellant and it is packed in a pressurized container. Suitable propellants are, for example, the lower alkanes, for example n-butane, isobutane and propane or mixtures thereof with dimethyl ether, furthermore propellants which at the pressures involved are gaseous, for example $N_2$, $N_2O$ and $CO_2$ and mixtures of the aforesaid propellants.

The hair-setting agents of the invention can also be in the form of a non-aerosol hair spray or non-aerosol coating sprayable by means of an appropriate mechanical spraying device. By mechanical spraying devices are meant devices which make it possible to spray a liquid without the use of a propellant. A suitable mechanical spraying device is, for example, a spray pump or an elastic container provided with a spray valve and in which the cosmetic agent of the invention is contained under pressure. This pressure causes the elastic container to expand so that, when the spray valve is opened, the agent is forced out continuously by the contraction of the elastic container.

By hair treatment is meant primarily the treatment of human hair for the purpose of providing a hair-do or for hair-grooming purposes.

The following examples illustrate the object of the invention in greater detail. The described hair fixatives are characterized, in particular, by the fact that they provide long-lasting hair setting. After the first hair washing, the polymer network continues to adhere to the hair which results in lasting hair fixation. Depending on the system chosen, three to five washings may be sufficient to restore the untreated hair condition.

EXAMPLES

EXAMPLE 1

| Hair Fixative | |
|---|---|
| 1.50 g | of inorganic-organic hybrid prepolysiloxane from 3-glycidoxypropyltrimethyloxysilane, 3-triethoxysilyl-propylsuccinic anhydride and 1-methylimidazole [system 1)] |
| 1.50 g | of vinylpyrrolidone-vinyl acetate copolymer |
| 0.20 g | of 1,2-propylene glycol |
| 0.15 g | of perfume |
| 0.03 g | of cetyltrimethylammonium chloride |
| 20.21 g | of water |
| 76.41 g | of ethanol |
| 100.00 g | |

Alternatively, any of the other above-described systems 2) to 10) can be used as the hybrid prepolymer.

EXAMPLE 2

| Hair Fixative | |
|---|---|
| 0.88 g | of inorganic-organic hybrid prepolysiloxane from mercaptopropyltriethoxysilane and hydrochloric acid [system 9)] |
| 2.63 g | of vinylpyrrolidone-vinyl acetate copolymer |
| 0.20 g | of 1,2-propylene glycol |
| 0.15 g | of perfume |
| 0.05 g | of cetyltrimethylammonium chloride |
| 59.89 g | of water |
| 46.28 g | of ethanol |
| 100.00 g | |

EXAMPLE 3

| Hair Fixative | |
|---|---|
| 4.88 g | of inorganic-organic hybrid prepolysiloxane from 3-glycidoxypropyltrimethoxysilane, tetramethoxysilane, tributoxyaluminum, tetrapropoxyzirconium and triethanolamine [system 3)] |
| 0.20 g | of 1,2-propylene glycol |
| 0.15 g | of perfume |
| 0.05 g | of cetyltrimethylammonium chloride |
| 49.71 g | of water |
| 45.01 g | of ethanol |
| 100.00 g | |

EXAMPLE 4

| UV Absorber-Containing Lotion for Use with Hair Dryer | |
|---|---|
| 1.80 g | of inorganic-organic hybrid prepolysiloxane from 3-glycidoxypropyltrimethoxysilane, trimethoxyphenyl-silane, 2,2,2-trifluoroethylamine, tributoxyaluminum and ethyl acetoacetate [system 4)] |
| 1.20 g | of polyvinylpyrrolidine |
| 0.20 g | of perfume |
| 0.15 g | of glycerol (85%) |

-continued

UV Absorber-Containing Lotion for Use with Hair Dryer

| | |
|---|---|
| 0.10 g | of 2-hydroxy-4-methoxybenzophenone |
| 61.30 g | of water |
| 35.25 g | of ethanol |
| 100.00 g | |

EXAMPLE 5

Hair-Grooming Fixative Lotion

| | |
|---|---|
| 2.12 g | of inorganic-organic hybrid prepolysiloxane from mercaptopropyltriethoxysilane and hydrochloric acid [system 9)] |
| 2.12 g | of vinylpyrrolidone-vinyl acetate copolymer |
| 0.40 g | of hydrogenated castor oil, ethoxylated with 40 moles of ethylene oxide |
| 0.20 g | of perfume |
| 95.16 g | of water |
| 100.00 g | |

EXAMPLE 6

High-Efficacy Foaming Fixative

| | |
|---|---|
| 2.00 g | of inorganic-organic hybrid prepolysiloxane from mercaptopropyltriethoxy-silane and hydrochloric acid [system 9)] |
| 2.00 g | of vinylpyrrolidone - methylaminoethyl methacrylate copolymer |
| 0.45 g | of glyceryl laurate |
| 0.15 g | of perfume |
| 0.16 g | of cetylatrimethylammonium chloride |
| 5.00 g | of propane/butane (5.0 bar) |
| 14.95 g | of ethanol |
| 75.29 g | of water |
| 100.00 g | |

EXAMPLE 7

Foaming Fixative

| | |
|---|---|
| 3.00 g | of inorganic-organic hybrid prepolysiloxane from 3-glycidoxypropyltrimethoxysilane, tetramethoxysilane, tributoxyaluminum, tetrapropoxyzirconium and triethanolamine [system 3)] |
| 1.00 g | of vinylpyrrolidone - methylaminoethyl methacrylate copolymer |
| 0.20 g | of 1,2-propylene glycol |
| 0.17 g | of perfume |
| 0.10 g | of cetyltrimethylammonium chloride |
| 6.00 g | of propane/butane (5.0 bar) |
| 18.66 g | of ethanol |
| 70.87 g | of water |
| 100.00 g | |

EXAMPLE 8

Foaming Fixative

| | |
|---|---|
| 4.00 g | of inorganic-organic hybrid prepolysiloxane from mercaptopropyltriethoxysilane and hydrochloric acid [system 9)] |
| 1.00 g | of inorganic-organic hybrid prepolysiloxane from 3-glycidoxypropyltrimethoxysilane, tetramethoxysilane, tributoxyaluminum, tetrapropoxyzirconium and triethanolamine [system 3)] |
| 0.20 g | of 1,2-propylene glycol |
| 0.17 g | of perfume |
| 0.10 g | of cetyltrimethylammonium chloride |
| 6.00 g | of propane/butane (5.0 bar) |
| 69.04 g | of ethanol |
| 19.49 g | of water |
| 100.00 g | |

EXAMPLE 9

Foaming Fixative for Grooming

| | |
|---|---|
| 1.12 g | of inorganic-organic hybrid prepolysiloxane from 3-glycidoxypropyltrimethoxysilane, aminosilane and 3-mercaptopropyltriethoxysilane [system 8)] |
| 3.40 g | of vinylcaprolactam-vinylpyrrolidone - dimethylaminoethyl methacrylate terpolymer |
| 0.60 g | of formic acid |
| 0.60 g | of hydrogenated castor oil ethoxylated with 40 moles of ethylene oxide |
| 0.22 g | of decylpolyglucoside |
| 0.09 g | of cetyltrimethylammonium chloride |
| 0.20 g | of perfume |
| 6.00 g | of propane/butane (5.0 bar) |
| 87.77 g | of water |
| 100.00 g | |

EXAMPLE 10

Styling Hair Spray

| | |
|---|---|
| 3.14 g | of inorganic-organic hybrid prepolysiloxane from mercaptopropyltriethoxysilane and hydrochloric acid [system 9)] |
| 1.50 g | of octylacrylamide-acrylic acid-butylaminoethyl methacrylate-hydroxypropyl methacrylate copolymer |
| 0.15 g | of perfume |
| 10.67 g | of butane (1.5 bar) |
| 33.33 g | of propane/butane |
| 51.21 g | of ethanol |
| 100.00 g | |

EXAMPLE 11

Pump Spray

| | |
|---|---|
| 2.79 g | of inorganic-organic hybrid prepolysiloxane from mercapto-propyltriethoxysilane, vinyl triethoxysilane and aqueous hydrochloric acid (1 N) [system 11)] |
| 0.30 g | of perfume |
| 0.10 g | of dimethylsiloxane - ethylene glycol copolymer |

-continued

Pump Spray

| | |
|---|---|
| 11.53 g | of water |
| 85.28 g | of ethanol |
| 100.00 g | |

EXAMPLE 12

80% VOC Hair Spray

| | |
|---|---|
| 1.63 g | of inorganic-organic hybrid prepolysiloxane from 3-glycidoxypropyltrimethoxysilane, tetramethoxysilane, tributoxyaluminum, tetrapropoxyzirconium and triethanolamine [system 3)] |
| 0.82 g | of inorganic-organic hybrid prepolysiloxane from mercaptopropyltriethoxysilane and hydrochloric acid [system 9)] |
| 4.00 g | of vinyl acetate-crotonic acid-polyethylene oxide copolymer |
| 0.20 g | of cyclotetra(dimethylsiloxane) |
| 0.15 g | of perfume |
| 13.20 g | of water |
| 40.00 g | of ethanol |
| 40.00 g | of dimethyl ether |
| 100.00 g | |

EXAMPLE 13

80% VOC Pump Spray

| | |
|---|---|
| 1.50 g | of inorganic-organic hybrid prepolysiloxane from mercaptopropyltriethoxysilane, vinyltriethoxysilane and aqueous hydrochloric acid (1 N) [system 11)] |
| 1.50 g | of inorganic-organic hybrid prepolysiloxane from 3-glycidoxypropyltrimethoxysilane, tetramethoxysilane, tributoxyaluminum, tetrapropoxyzirconium and triethanolamine [system 3)1 |
| 5.00 g | of vinyl acetate-crotonic acid-polyethylene oxide copolymer |
| 0.30 g | of perfume |
| 11.70 g | of water |
| 80.00 g | of ethanol |
| 100.00 g | |

EXAMPLE 14

55% VOC Pump Spray

| | |
|---|---|
| 4.00 g | of inorganic-organic hybrid prepolysiloxane from 3-glycidoxypropyltrimethoxysilane, tetramethoxysilane, tributoxyaluminum, tetrapropoxyzirconium and triethanolamine [system 3)] |
| 0.20 g | of perfume |
| 40.80 g | of water |
| 55.00 g | of ethanol |
| 100.00 g | |

EXAMPLE 15

Hair Gel

| | |
|---|---|
| 2.76 g | of inorganic-organic hybrid prepolysiloxane from 3-glycidoxypropyltrimethoxysilane, trimethoxyphenylsilane, aminosilane, tributoxyaluminum and tetrapropoxyzirconium [system 7)] |
| 0.40 g | of polyacrylic acid |
| 0.10 g | of hydroxypropylmethylcellulose |
| 0.80 g | of polyoxyethylene-(20)-sorbitan monopalmitate |
| 0.50 g | of polyoxyethylene-(25)-p-aminobenzoic acid |
| 0.12 g | of cis-1-(3-chloroallyl)-3,5,7-triaza-1-azoniaadamantane chloride |
| 0.10 g | of perfume |
| 23.00 g | of glycerol (86%) |
| 72.22 g | of water |
| 100.00 g | |

EXAMPLE 16

Setting Hair Styling Gel

| | |
|---|---|
| 1.53 g | of inorganic-organic hybrid prepolysiloxane from mercaptopropyltriethoxysilane and hydrochloric acid [system 9)] |
| 2.50 g | of polyvinylpyrrolidone |
| 2.10 g | of hydroxypropylguar |
| 0.80 g | of hydrogenated castor oil ethoxylated with 45 moles of ethylene oxide |
| 0.45 g | of sodium benzoate |
| 0.30 g | of hydroxyethylcellulose |
| 0.20 g | of perfume |
| 0.09 g | of sodium formate |
| 0.05 g | of mica-titanium oxide-tin oxide powder (Soloron ® Silver Sparkle, supplied by Merck, Germany) |
| 91.98 g | of water |
| 100.00 g | |

EXAMPLE 17

Hair-Setting Liquid Gel

| | |
|---|---|
| 2.95 g | of inorganic-organic hybrid prepolysiloxane from 3-glycidoxypropyltrimethxysilane, tetramethoxysilane, tributoxyaluminum, tetrapropoxyzirconium and triethanolamine [system 3)] |
| 0.35 g | of polyacrylic acid |
| 0.15 g | of hydroxyethylcellulose |
| 0.26 g | of 2-aminopropanol |
| 1.80 g | of polyoxyethylene-(20)-sorbitan monopalmitate |
| 1.35 g | of polyethylene glycol-(45) |
| 1.05 g | of hydroxyethylcellulose |
| 0.20 g | of 1,2-dibromo-2,4-dicyanobutane |
| 0.30 g | of perfume |
| 91.59 g | of water |
| 100.00 g | |

The aforesaid agents, if they are liquid fixatives or lotions, are used by applying them to and uniformly spreading them on the towel-dry hair. The hair-do is made, and the hair is dried for 15 to 20 min with a hair dryer running at the medium heat setting or with a thermostattable hair dryer at 40 to 50° C.

The use of gels and sprays involves first washing the hair, making the hair-do and drying the hair, after which the gel or spray is applied to the dry hair. The hair is then dried in air or, for 15 to 20 min, with a hair dryer running at the medium heat setting or with a thermostattable hair dryer at 40 to 50° C.

EXAMPLE 18

Hair-Dryer Lotion with UV Absorber

| | |
|---|---|
| 1.40 g | of inorganic-organic hybrid prepolymer from mercaptopropyltriethoxysilane, vinyltriethoxysilane and aqueous hydrochloric acid (1 N) [system 11)] |
| 1.50 g | of vinylpyrrolidone-vinyl acetate copolymer |
| 0.20 g | of perfume |
| 0.15 g | of glycerol (85%) |
| 0.10 g | of 2-hydroxy-4-methoxybenzophenone |
| 42.90 g | of water |
| 51.60 g | of ethanol |
| 100.00 g | |

EXAMPLE 19

Hair-Dryer Lotion with Antidandruff Action

| | |
|---|---|
| 1.40 g | of inorganic-organic hybrid prepolymer from 3-glycidoxypropyltrimethoxysilane, tetramethoxysilane, tributoxyaluminum, tetrapropoxyzirconium and triethanolamine [system 3)] |
| 1.50 g | of vinylpyrrolidone-vinyl acetate copolymer |
| 0.20 g | of perfume |
| 1.15 g | of 1,2-propylene glycol |
| 0.40 g | of 1-hydroxy-4-methyl-6-(2,4,4-trimethylpentyl)-2(1H) pyridone monoethanolamine salt |
| 42.60 g | of water |
| 50.60 g | of ethanol |
| 100.0 g | |

EXAMPLE 20

Color Fixative

| | |
|---|---|
| 0.23 g | of inorganic-organic hybrid prepolymer from mercaptopropyltriethoxysilane and hydrochloric acid [system 9)] |
| 2.50 g | of vinyl acetate-crotonic acid-polyglycol copolymer |
| 0.20 g | of perfume |
| 0.07 g | of 1-amino-4-(2',3'-dehydroxypropyl)amino-5-chloro-2-nitrobenzene |
| 0.05 g | of Basic Brown 17 (C.I. 12 251) |
| 0.01 g | of Basic Blue 7 (C.I. 42 595) |
| 0.0023 g | of Basic Violet 14 (C.I. 42 510) |
| 46.94 g | of water |
| 50.00 g | of ethanol |
| 100.0 g | |

EXAMPLE 21

Color Fixative

| | |
|---|---|
| 1.23 g | of inorganic-organic hybrid prepolymer from mercaptopropyltriethoxysilane, vinyltriethoxysilane and aqueous hydrochloric acid (1 N) [system 11)] |
| 1.50 g | of vinyl acetate-crotonic acid copolymer |
| 0.20 g | of perfume |
| 0.09 g | of 3-{[(2-nitro-4-(trifluoromethyl)phenyl]amino}-1,2-propanediol |
| 46.94 g | of water |
| 50.08 g | of ethanol |
| 100.0 g | |

EXAMPLE 22

Hair Fixative

| | |
|---|---|
| 1.23 g | of inorganic-organic hybrid prepolymer from 3-glycidoxypropyltrimethoxysilane, tetramethoxysilane, tributoxyaluminum, tetrapropoxyzirconium and triethanolamine [system 3)] |
| 1.50 g | of vinyl acetate-crotonic acid-polyglycol copolymer |
| 0.20 g | of perfume |
| 19.092 g | of Colorona Carmine Red |
| 38.04 g | of water |
| 40.00 g | of ethanol |
| 100.0 g | |

EXAMPLE 23

Foaming Color Fixative

| | |
|---|---|
| 3.00 g | of inorganic-organic hybrid silane prepolymer from 3-glycidoxypropyltrimethoxysilane, tetramethoxysilane, tributoxyaluminum, tetrapropoxyzirconium and triethanolamine [system 3)] |
| 1.00 g | of vinylpyrrolidone-methylaminoethyl methacrylate copolymer |
| 0.07 g | of 1-amino-4-(2',3'-dehydroxypropyl)amino-5-chloro-2-nitrobenzene |
| 0.05 g | of Basic Brown 17 (C.I. 12 251) |
| 0.01 g | of Basic Blue 7 (C.I. 42 595) |
| 18.66 g | of ethanol |
| 70.74 g | of water |
| 100.0 g | |

EXAMPLE 24

Foaming Color Fixative

| | |
|---|---|
| 3.00 g | of inorganic-organic hybrid prepolymer from 3-glycidoxypropyltrimethoxysilane, tetramethoxysilane, tributoxyaluminum, tetrapropoxyzirconium and triethanolamine [system 3)] |
| 1.00 g | of vinylpyrrolidone - methylaminoethyl methacrylate copolymer |
| 0.11 g | of 3-{[(2-nitro-4-(trifluoromethyl)phenyl]amino}-1,2-propanediol |
| 0.20 g | of 1,2-propylene glycol |
| 0.17 g | of perfume |
| 0.10 g | of cetyltrimethylammonium chloride |
| 6.00 g | of propane/butane (5.0 bar) |

EXAMPLE 25

| Foaming Color Fixative | |
|---|---|
| 3.00 g | of inorganic-organic hybrid prepolymer from 3-glycidoxy-propyltrimethoxysilane, tetramethoxysilane, tributoxyaluminum, tetrapropoxyzirconium and triethanolamine [system 3)] |
| 1.00 g | of vinylpyrrolidone-methylaminoethyl methacrylate copolymer |
| 20.10 g | of Colorona Carmine Red |
| 0.20 g | of 1,2-propylene glycol |
| 0.17 g | of perfume |
| 0.10 g | of cetyltrimethylammonium chloride |
| 6.00 g | of propane/butane (5.0 bar) |
| 18.66 g | of ethanol |
| 50.77 g | of water |
| 100.0 g | |

EXAMPLE 26

| Hair Color Gel | |
|---|---|
| 2.76 g | of inorganic-organic hybrid prepolymer from 3-glycidoxy-propyltrimethoxysilane, tetramethoxysilane, tributoxyaluminum, tetrapropoxyzirconium and triethanolamine [system 3)] |
| 0.40 g | of polyacrylic acid |
| 0.10 g | of hydroxypropylmethylcellulose |
| 0.80 g | of polyoxyethylene-(20)-sorbitan monopalmitate |
| 0.50 g | of polyoxyethylene-(25)-p-aminobenzoic acid |
| 0.12 g | of cis-1-(3-chloroallyl)-3,5,7-triaza-1-azoniaadamantane chloride |
| 20.20 g | of Colorona Carmine Red |
| 0.10 g | of perfume |
| 18.00 g | of glycerol (86%) |
| 57.22 g | of water |
| 100.0 g | |

EXAMPLE 27

| Colorless Nail Polish | |
|---|---|
| 6.0 g | of inorganic-organic hybrid prepolymer from 3-glycidoxy-propyltrimethoxysilane, tetramethoxysilane, tributoxyaluminum, tetrapropoxyzirconium and triethanolamine [system 3)] |
| 18.0 g | of nitrocellulose (alcohol-wet, 65:35) |
| 4.0 g | of dibutyl phthalate |
| 2.0 g | of camphor |
| 40.0 g | of butyl acetate |
| 30.0 g | of ethyl acetate |
| 100.0 g | |

EXAMPLE 28

| Colored Nail polish | |
|---|---|
| 6.0 g | of inorganic-organic hybrid prepolymer from 3-glycidoxy-propyltrimethoxysilane, tetramethoxysilane, tributoxyaluminum, tetrapropoxyzirconium and triethanolamine [system 3)] |
| 4.0 g | dibutyl phthalate |
| 2.0 g | of tricresyl phosphate |
| 20.0 g | of ethylene glycol monomethyl ether |
| 2.0 g | of diethylene glycol monomethyl ether |
| 28.0 g | of methylene chloride |
| 14.5 g | of ethanol |
| 9.0 g | of butyl acetate |
| 6.0 g | of ethyl acetate |
| 2.5 g | of Colorona Carmine Red |
| 100.0 g | |

What is claimed is:

1. A cosmetic composition comprising
at least one inorganic-organic hybrid prepolymer having an Si—O—S network and made by hydrolytic precondensation of at least one organofunctional silane of formula (I):

$$RSiX_3 \qquad (I),$$

wherein R represents a crosslinkable organic group selected from the group consisting of alkyl, alkenyl, alkynyl, aryl, arylalkyl, alkylaryl, arylalkenyl, alkenylaryl, arylalkynyl, and alkynylaryl crosslinkable groups, and wherein said alkyl, alkenyl, alkynyl, aryl, arylalkyl, alkylaryl, arylalkenyl, alkenylaryl, arylalkynyl and alkynylaryl crosslinkable groups may optionally be interrupted by at least one O, S, or N atom, OR wherein R denotes an organic group that is not crosslinkable by itself but contains a crosslinkable substituent and said crosslinkable substituent is selected from the group consisting of halogen, amino, amido, aldehyde, keto, alkylcarbonyl, carboxy, mercapto, cyano, hydroxyl, alkoxy, methacryloxy, epoxy, and vinyl groups; and wherein X denotes a hydrolyzable and condensable group selected from the group consisting of hydrogen, alkoxy, aryloxy, acyloxy, alkylcarbonyl, alkoxycarbonyl, halogen and substituted or unsubstituted amino groups; and and at least one cosmetic ingredient selected from the group consisting of water, organic solvents, non-setting nonionic polymers, non-setting anionic polymers, non-setting natural polymers, thickeners, perfumes, opacifers, anionic surfactants, cationic surfactants, amphoteric surfactants, nonionic surfactants, humectants, colorants, dyes, light-stabilizers, antioxidants, preservatives, propellants, and silicone polymers.

2. The cosmetic composition as defined in claim 1, containing from 0.01 to 40 percent by weight of said at least one inorganic-organic hybrid prepolymer.

3. The cosmetic composition as defined in claim 1, wherein said hydrolytic precondensation occurs in the presence of at least one condensation catalyst.

4. The cosmetic composition as defined in claim 1, further comprising at least one film-forming, hair-setting polymer.

5. A cosmetic composition comprising
at least one inorganic-organic hybrid prepolymer having an Si—O—S network and made by hydrolytic precondensation of a network-modifying compound and at least one organofunctional silane of formula (I):

$$RSiX_3 \qquad (I),$$

wherein said network modifying compound is an alkyl, alkoxy, halogen, acyloxy, hydroxy, oxyhalogen or hydroxyhalogen compound of a transition metal or a Group IIIA metal, $SiX_4$ or $SiR'XR$;

wherein R' represents an alkyl or an aryl group;

wherein R represents a crosslinkable organic group selected from the group consisting of alkyl, alkenyl, alkynyl, aryl, arylalkyl, alkylaryl, arylalkenyl, alkenylaryl, arylalkynyl, and alkynylaryl crosslinkable groups, and wherein said alkyl, alkenyl, alkynyl, aryl, arylalkyl, alkylaryl, arylalkenyl, akenylaryl, arylalkynyl and alkynylaryl crosslinkable groups may optionally be interrupted by at least one O, S or N atom, OR wherein R denotes an organic group that is not crosslinkable by itself but contains a crosslinkable substituent and said crosslinkable substituent is selected from the group consisting of halogen, amino, aldehyde, keto, alkylcarbonyl, carboxy, mercapto, cyano, hydroxyl, alkoxy, methacryloxy, epoxy, and vinyl groups; and wherein X denotes a hydrolyzable and condensable group selected from the group consisting of hydrogen, alkoxy, aryloxy, acyloxy, alkylcarbonyl, alkoxycarbonyl, halogen and substituted or unsubstituted amino groups; and at least one cosmetic ingredient selected from the group consisting of water, organic solvents, non-setting non-ionic polymers, non-setting anionic polymers, non-setting natural polymers, thickeners, perfumes, opacifers, anionic surfactants, cationic surfactants, amphoteric surfactants, nonionic surfactants, humectants, colorants, dyes, light-stabilizers, anti-oxidants, preservatives, propellants, and silicone polymers.

6. The cosmetic composition as defined in claim 5, wherein said network modifying compound is an alkyl, alkoxy, halogen, acyloxy, hydroxy, oxyhalogen or hydroxyhalogen compound of a Group IVB metal.

7. The cosmetic composition as defined in claim 6, wherein said Group IVB metal is titanium or zirconium.

8. The cosmetic composition as defined in claim 5, wherein said network modifying compound is an alkyl, alkoxy, halogen, acyloxy, hydroxy, oxyhalogen or hydroxyhalogen compound of aluminum.

9. The cosmetic composition as defined in claim 5, containing from 0.01 to 40 percent by weight of said at least one inorganic-organic hybrid prepolymer.

10. The cosmetic composition as defined in claim 5, further comprising at least one film-forming, hair-setting polymer.

11. The cosmetic composition as defined in claim 1 or 5, wherein said at least one inorganic-organic hybrid prepolymer is formed by hydrolytically condensing a reactant mixture selected from the group consisting of mixtures of 3-glycidoxypropyltrimethoxysilane, 3-triethoxysilylpropylsuccinic anhydride and 1-methylimidazole; mixtures of 3-glycidoxypropyltrimethoxysilane, trimethoxyphenylsilane, an aminosilane, tributoxyaluminum and ethylacetoacetate; mixtures of 3-glycidoxypropyltrimethoxysilane, tetramethoxysilane, tributoxyaluminum, tetrapropoxyzirconium and triethanolamine; mixtures of 3-glycidoxypropyltrimethoxysilane, trimethoxyphenylsilane, 2,2,2,-trifluoroethylamine, tributoxyaluminum and ethyl acetoacetate; mixtures of 3-methacryloxypropyltrimethoxysilane and tetrapropoxyzirconium in the presence of a UV or thermal initiator; mixtures of 3-glycidoxpropyltrimethoxysilane, trimothoxyphenylsilane, an aminosilane, tributoxyaluminum and ethylacetoacetate; mixtures of 3-glycidoxypropyltrimethoxysilane, trimethoxyphenylsilane, an aminosilane, tributoxyaluminum and tetrapropoxyzirconium; mixtures of 3-glycidoxypropyltrimethoxysilane, an aminosilane and 3-mercaptotriethoxysilane; mixtures of mercaptopropyltriethoxysilane and hydrochloric acid (1N); mixtures of 3-glycidoxypropyltrimethoxysilane, trimethoxyphenysilane, tributoxyaluminum and ethylacetoacetate and mixtures of mercaptopropyltriethoxysilane and vinyltriethoxysilane.

12. A method for treating hair, said method comprising the steps of:

a) applying to hair an effective amount of a cosmetic composition comprising at least one cosmetic ingredient and at least one as-yet-uncrosslinked hydrolytic precondensation product for forming an inorganic-organic hybrid polymer; and b) after the applying of step a), crosslinking said as-yet-uncrosslinked hydrolytic precondensation product while said as-yet-uncrosslinked hydrolytic precondensation product remains on the hair to form said inorganic-organic hybrid polymer;

wherein said as-yet-uncrosslinked hydrolytic precondensation product has an Si—O—S network and is made by a process comprising hydrolytic precondensation of at least one organofunctional silane of formula (I):

$$RSiX_3 \qquad (I),$$

wherein R represents a crosslinkable organic group selected from the group consisting of alkyl, alkenyl, alkynyl, aryl, arylalkyl, alkylaryl, arylalkenyl, alkenylaryl, arylalkynyl, and alkynylaryl, crosslinkable groups, and wherein said alkyl, alkenyl, alkynyl, aryl, arylalkyl, alkylaryl, arylalkenyl, alkenylaryl, arylalkynyl and alkynylaryl crosslinkable groups may optionally be interrupted by at least one O, S or N atom, OR wherein R denotes an organic group that is not crosslinkable by itself but contains a crosslinkable substituent and said crosslinkable substituent is selected from the group consisting of halogen, amino, amido, aldehyde, keto, alkylcarbonyl, carboxy, mercapto, cyano, hydroxyl, alkoxy, methacryloxy, epoxy an vinyl groups; and wherein X denotes a hydrolyzable and condesable group selected from the group consisting of hydrogen, alkoxy, aryloxy, acyloxy, alkylcarbonyl, alkoxycarbonyl, halogen and substituted or unsubstituted amino groups; and wherein said at least one cosmetic ingredient is selected from the group consisting of water, organic solvents, non-setting nonionic polymers, non-setting anionic polymers, non-setting natural polymers, thickeners, perfumes, opacifers, anionic surfactants, cationic surfactants, amphoteric surfactants, nonionic surfactants, humectants, colorants, dyes, light-stabilizers, anti-oxidants, preservatives, propellants and silicone polymers.

13. The method as defined in claim 12, wherein, prior to said hydrolytic precondensation, said at least one organofunctional silane of the formula (I) is combined with at least one network-modifying compound and said at least one network-modifying compound is an alkyl, alkoxy, halogen, acyloxy, hydroxy, oxyhalogen or hydroxyhalogen compound of a transition metal or a Group IIIA metal, $SiX_4$ or SiR'XR; wherein R' represents an alkyl or an aryl group.

14. The method as defined in claim 12, wherein said at least one organofunctional silane of formula (I) is selected from the group consisting of vinyltrialkoxysilanes, vinyltriaectoxysilane, aminopropyltrialkoxysilanes, isocyanatopropyltrialkoxysilanes, mercaptopropyltrialkoxysilanes, vinyltrichlorosilane, allyltrialkoxysilanes, allyltriacetoxysilane, 3-isocyanatooxypropyltrialkoxysilanes, methacryloxypropenyltrialkoxysilanes, 3-methacrylcarbonyloxypropyltrialkoxysilanes, p-aminophenyltrialkoxysilanes, 3-aminopropyltrialkoxysilanes, 3-cyanopropyltrialkoxy silanes, 4-mercaptobutyltrialkoxysilanes, 6-mercaptohexyltrialkoxysilanes, 3-mercaptopropyltrialkoxysilanes, 3-(ethylenediamino) propyltrialkoxysilanes, 3-(diethylenetriamino)-propylalkoxysilanes, 3-glycidoxypropyltrialkoxysilanes, 2-[4-(1,2-epoxycyclohexyl)]ethyltrialkoxysilanes and 3-(trialkoxysilyl)propylsuccinic anhydride; and wherein alkoxy represents either methoxy or ethoxy.

* * * * *